(12) United States Patent
Higashi et al.

(10) Patent No.: US 6,765,667 B2
(45) Date of Patent: Jul. 20, 2004

(54) METHOD FOR INSPECTION OF CIRCUIT BOARDS AND APPARATUS FOR INSPECTION OF CIRCUIT BOARDS

(75) Inventors: Noboru Higashi, Matsuyama (JP); Daisuke Nagai, Ehime (JP); Kenichi Kaida, Matsuyama (JP)

(73) Assignee: Matsushita Electric Industrial Co., Ltd., Osaka (JP)

( * ) Notice: Subject to any disclaimer, the term of this patent is extended or adjusted under 35 U.S.C. 154(b) by 376 days.

(21) Appl. No.: 09/916,181

(22) Filed: Jul. 26, 2001

(65) Prior Publication Data

US 2002/0024660 A1 Feb. 28, 2002

(30) Foreign Application Priority Data

Jul. 27, 2000 (JP) ........................................ 2000-227790

(51) Int. Cl.[7] .............................................. G01N 21/00
(52) U.S. Cl. .................................................. 356/237.4
(58) Field of Search .......................... 356/237.1–237.6, 356/239.1–239.8, 600–622; 324/760–765, 754, 158.1; 361/797, 798, 752, 683

(56) References Cited

U.S. PATENT DOCUMENTS 6,496,025 B1 * 12/2002 Stadelmayer et al. ....... 324/761
6,549,025 B1 * 4/2003 Tubera et al. ............... 324/760
6,591,389 B1 * 7/2003 Daudelin et al. ........... 714/733

FOREIGN PATENT DOCUMENTS

JP              04208803 A           7/1992

* cited by examiner

Primary Examiner—Tu T. Nguyen
(74) Attorney, Agent, or Firm—Akin Gump Strauss Hauer & Feld, L.L.P.

(57) ABSTRACT

A method for inspection of circuit boards is described which includes: a process of measuring surface-shape data of a circuit board on which inspection objects are placed; an approximated curved surface generation process for generating an approximated curved surface from the measured surface-shape data, which is an estimated surface-shape of the circuit board, on which no inspection object is placed; a process of subtracting said approximated curved surface from the measured surface-shape data; a region of interest determination process of determining regions which are different from the approximated curved surface in accordance with data obtained by said subtraction process; and a process of inspecting whether electronic parts placed on said circuit board and connecting materials for connecting the electronic parts are in a desired state or not.

18 Claims, 3 Drawing Sheets

METHOD FOR INSPECTION OF CIRCUIT BOARDS AND APPARATUS FOR INSPECTION OF CIRCUIT BOARDS

BACKGROUND OF THE INVENTION

The present invention relates to an inspection method for inspecting circuit boards (printed circuit board: PCB) by the image processing, in particular, with respect to circuit boards installed in consumers appliances or electronic apparatus such as computers, and relates to the inspection method for inspecting parts in the circuit board and solders connecting those parts, There are circuit board visual inspection instruments as the inspection apparatus for inspecting the appearance of circuit boards to be installed in electronic apparatus. The circuit board visual inspection instruments are broadly classified into two classes depending upon the image-picture taking method. One is a 2-dimensional imaging apparatus that is a combination of a CCD camera and a lighting apparatus (special lighting apparatus devising light illumination state using such as a ring-shaped light source), and the other is a 3-dimensional imaging apparatus based on the laser trigonometrical survey or the light-section method.

In the conventional circuit board inspection method, in case of implementing the visual inspection of parts installed on an electronic circuit board in accordance with image data obtained by the measurements using the above-mentioned 2-dimensional imaging apparatus or the 3-dimensional imaging apparatus, a region to be inspected, such as a region of interest, ROI, for each part has been set, and then only the ROI for each part has been inspected.

On the other hand, as for an apparatus for inspecting the whole plane of a circuit board, there is an inspection apparatus disclosed in Japanese Unexamined Patent Application Gazette, Hei 4-208803. In this inspection apparatus, from spatial information at three points at which no part is installed on a circuit board, inclination of this circuit board is detected. In this latter conventional inspection apparatus, calculation is made on a plane that was in parallel with respect to the circuit board as the board-approximated plane, and then having this boardapproximated plane as a threshold value, measured image data were converted into binary data; thereby a binary image data was obtained. In this conventional inspection apparatus, based on obtained binary image data, size, position, and inclination of each parts were calculated, and then the results are compared with predetermined standard values, and thereby the installation state of each part on the board were inspected. In such a manner, in accordance with the inspection apparatus disclosed in the Unexamined Patent Application Gazette, Hei 4-208803, it was possible to inspect the whole plane of a circuit board.

In the aforementioned circuit board visual inspection apparatus using one of conventional circuit board inspection methods, inspection regions are previously set up, and inspection was carried out on only those pre-set regions, whereas no inspection was done on other regions than those set regions; as a result, in those cases that electronic parts and solders were placed mistakenly in those regions other than pre-set regions, these were not detected. There was a problem that any inadequate placement of electronic parts and solders could be the cause that would introduce short-circuiting between wirings or abnormal actions, thereby extremely lowering the quality of the circuit board extremely. That is, in those conventional circuit board visual inspection apparatus in which the inspection regions were limited, there was a problem that any cause of the failure as mentioned above, could not be detected.

As the apparatus which solves such the problem in the conventional circuit board visual inspection, there was an inspection apparatus disclosed in the Unexamined Patent Application Gazette, Hei 4-208803, in which the inspection of the parts installation state in the whole area of a circuit board was carried out. In this inspection apparatus, a method was proposed that an approximated plane of a circuit board was calculated as a threshold value from three points at which no part is installed on a circuit board, then condition of the installed part is extracted from this threshold value and the threedimensional information. In accordance with this method, when the heights of the parts that were the objects of the inspection was higher enough than the amount of the deformation of the circuit board, it was possible to extract the electronic parts and solders by the comparison between the three dimensional information of the circuit board and the approximated plane. However, since an actual circuit board has a three-dimensional deformation, in such cases as for miniature-sized parts wherein heights of the inspection objects are lower with respect to the deformation of the circuit board, such the miniaturesized parts are buried by the deformation of the circuit board, it happened that such the miniaturesized parts could not be extracted by the comparison process with respect to the approximated plane. And at those positions where the amount of the deformation of the circuit board is large, it also happened that the circuit board itself was recognized by mistake as the parts of object to be inspected. Particularly, in case of inspecting the miniature-sized parts, which were the trend of recent years, and the printed solder-pastes for connecting those parts, it was not possible to realize a high accuracy extraction of them.

Then, in the present invention proposed here, which proposes a circuit board inspection method which enables to extract, in high accuracy, all the miniature-sized parts placed on a circuit board excluding the influence due to the amount of deformation of the circuit board, it purposes to improve the accuracy of the inspection.

BRIEF SUMMARY OF THE INVENTION

A circuit board inspection method in accordance with the present invention comprises:

(1) a step of measuring the 3-dimensional shape of a circuit board, which is the object of the inspection, thereby setting the data obtained to be surface-shape measured data, (2) a step of automatically estimating the amount of distortion of the circuit board from the surface-shape measured data of the whole surface of the measured circuit board, (3) a step of automatically generating an approximated surface shape from the estimated result at the above-mentioned step (2), and (4) a step of performing a subtraction process between the approximated surface generated at the above-mentioned step (3) and the surface-shape measured data.

The circuit board inspection apparatus is provided with processing apparatus performing the above-mentioned processing steps, thereby extracting in high accuracy those parts other than the circuit board which are placed on the whole surface of the circuit board. Then the circuit board inspection method and the apparatus using this method can carry out the inspection of circuit board in high accuracy by comparing the extracted data with respect to a preset teaching data showing position information and shape information of objects to be inspected in the qualified condition.

The circuit board inspection method in accordance with the present invention comprises:

- a measuring process for measuring the surface-shape data of the circuit board on which parts to be measured are placed,
- an approximated surface-shape generating process for generating an approximated surface-shape, which is estimating the surface-shape of a circuit board on which objects of interest are not placed, from measured surface-shape data,
- a subtraction process for subtracting the approximated surface-shape generated above from the measured surface-shape data,
- an ROI (region of interest) determination process for determining those areas which are different from the approximated surface-shape in accordance with the data obtained by the abovementioned subtraction process to be an ROI (region of interest), and
- an inspection process for inspecting if electronic parts placed on the above-mentioned circuit board as well as connecting materials for connecting those electronic parts are in a desired state with respect to the determined ROI.

As a result, in the method for inspection of circuit boards in accordance with the present invention, it becomes possible to recognize the objective parts to be inspected placed on a circuit board in high accuracy without being influenced by the distortion of the circuit board by the help of an approximated surface-shape which is approximating the circuit board surface, thereby a high accuracy inspection for the whole surface of the circuit board can be realized.

A circuit board inspection method in another aspect of the invention comprises:

- a histogram generating process in which the abovementioned approximated surface-shape generating process divides measured data of the surface-shape of a circuit board into smaller regions, and generates a histogram in the measured data for the surface-shape in those individual regions,
- a circuit board height determination process for determining circuit board heights at predetermined particular coordinate points in respective individual regions from the histogram generated, and
- an approximated surface-shape generating process for determining the circuit board height values at other coordinate points than those predetermined coordinate points at which the circuit board height values were already determined by an interpolating process using those already determined height values.

As a result, the method for inspection of circuit boards in accordance with the present invention has a function for generating automatically an approximated surface-shape for the circuit board surface from the surface-shape data of the circuit board on which objects of interest are placed.

In a circuit board inspection method in another aspect of the invention, the above-mentioned histogram generating process comprises:

- a process for measuring the amount of reflected light from the circuit board,
- an area determination process for determining those areas showing a particular light intensity in measured reflected light amount data, and
- a histogram generating process in which, using only those determined areas showing the particular light intensity, a histogram of surfaceshape data for those areas is generated.

As described above, in the method for inspection of circuit boards of the present invention, masking parts of the surface-shape data of the electronic parts, and generating a histogram by using only such data as in areas having higher probability to be the surface of the circuit board itself, thereby the circuit board height is determined with a higher accuracy. And, in the circuit board inspection method of the present invention determines, by masking the parts of interest, the circuit board height can be determined in high accuracy without being dependent on sizes of parts.

In a circuit board inspection method in another aspect of the invention, the above-mentioned histogram generating process comprises:

- a process of measuring the color information of the circuit board, and
- a process in which, using only such areas showing a particular color information in the above measured color information, a histogram of the surface shape data on that area is generated.

As has been stated above, the circuit board inspection method of the present invention is, utilizing the difference of colors of the surface of the circuit board, and masking the surface-shape data of electronic parts, then by generating the histogram using only those data at a particular portion wherein the probability is high over the electronic circuit, the surface height of the circuit board is determined in higher accuracy. And, in the circuit board inspection method of the present invention determines, by masking the parts of interest, the circuit board height can be determined in high accuracy without being dependent on sizes of parts.

In a circuit board inspection method in another aspect of the invention, the above-mentioned histogram generating process comprises a process in which, using only particular areas in CAD data of the circuit board, a histogram of the surface shape data on that area is generated. As has been stated above, the circuit board inspection method of the present invention is, masking the surface-shape data of electronic parts, then by generating the histogram using only those data at a particular portion wherein the probability is high over the circuit board surface, the surface height of the circuit board is determined in higher accuracy. And, in the circuit board inspection method of the present invention determines, by masking the parts of interest, the circuit board heights can be determined in high accuracy without being dependent on sizes of parts.

In a circuit board inspection method in another aspect of the invention, the above-mentioned area determination process comprises:

- a process for generating a histogram in data of the reflection light amount,
- a process for determining threshold values by which the histogram regions are divided using the histogram,
- a process by which, using the determined threshold values, data of the reflection light amount are area-divided, and
- a process for determining those areas having data of a particular light amount.

As a result, areas of particular parts can be extracted from the data of reflection light amount for the circuit board.

In a circuit board inspection method in another aspect of the invention, the above-mentioned board height determination process determines the maximum value of the histogram as the board height value. As a result, the circuit board inspection method of the present invention automatically determines the circuit board height values in divided regions from the histogram of the surface-shape data.

In a circuit board inspection method in another aspect of the invention, an approximated curve of the histogram is obtained, and then the maximum value of the histogram is determined as the board height value. As a result, in the circuit board inspection method of the present invention, the circuit board height can be determined in high accuracy.

In a circuit board inspection method in another aspect of the invention, in the above-mentioned process in which the height of the whole surface is obtained by an interpolation process, the whole surface of the circuit board is approximated to a curved surface by a higher order interpolation process, thereby it is determined as an approximated curved surface. As a result, in the circuit board inspection method of the present invention, the circuit board height can be determined in high accuracy.

In a circuit board inspection in another aspect of the invention, for the above-mentioned approximated curved surface generating process, making a curved surface obtained by adding an offset value to the approximated curved surface generated above to be a new approximated curved surface, and then using this approximated curved surface, the subtraction process is made. As a result, in the circuit board inspection method of the present invention, noise generated under various conditions is suppressed, thereby the recognition accuracy of the parts of interest can be improved.

In a circuit board inspection method in another aspect of the invention, for the abovementioned ROI determination process, the a real values of respective ROI obtained by the above-mentioned subtraction process is calculated, and only those regions that are in a predetermined range are determined as ROI. As a result, the circuit board inspection method of the present invention can eliminate those regions which were recognized faultily by the subtraction process.

In a circuit board inspection method in another aspect of the invention, the above-mentioned ROI determination process comprises reduction and expansion processes, as well as a process of eliminating the minute regions with respect to respective ROI obtained by the above-mentioned subtraction process. As a result, the method for inspection of circuit boards of the present invention determines can eliminate those areas which were recognized faultily by the subtraction process. And, in the circuit board inspection method in another aspect of the invention, in case that the shape of ROI is concave, those regions which could not be recognized in that ROI can be supplemented.

And, in a circuit board inspection method in another aspect of the invention, the above-mentioned ROI determination process comprises:
a process for expanding the ROI,
a process for separating the expanded ROI to a ROI and a board surface region, and
a process for performing the inspection for the separated ROI.

As a result, the circuit board inspection method of the present invention is a process in which, in order to exclude the error in the approximated curved surface, the ROI is extracted once again in minute region in the vicinity of determined ROI, and thereby ROI can be extracted in high accuracy.

In a circuit board inspection method in another aspect of the invention, ROI determined in the above-mentioned ROI determination process are made to be a teaching data which set an inspection reference. As a result, in the circuit board inspection method of the present invention, the setting of the teaching data regions which was set by hands in the conventional method can be made to be an automatic setting process.

And, by combining a plural numbers of circuit board inspection methods, a high-accurate circuit board inspection method can be offered.

A circuit board inspection apparatus in accordance with the present invention comprises:
a measuring section for measuring the data of the surface-shape of the circuit board on which objects of interest are placed,
an approximated surface-shape generating section for generating an approximated surface-shape, which is estimating a surface-shape of a circuit board on which parts of interest are not placed, from measured surface-shape data,
a subtraction section for subtracting the approximated surface-shape generated above from the measured surface-shape data,
an ROI determination section for determining those regions which are different from the approximated surface-shape in accordance with the data obtained by the above-mentioned subtraction process, and
an inspection sections for inspecting if the above-mentioned electronic parts placed on the circuit board as well as connecting materials for connecting those electronic parts are in a desired state with respect to the determined ROI.

As a result, by the circuit boards inspection apparatus in accordance with the present invention, it becomes possible to recognize the parts of interest placed on the circuit board in high accuracy without being influenced by the deformation of the circuit board by the help of an approximated curved surface which is approximating the circuit board surface, thereby a high accuracy inspection for the whole surface of the circuit board can be realized.

While the novel features of the invention are set forth particularly in the appended claims, the invention, both as to organization and content, will be better understood and appreciated along with other objects and features thereof from the following detailed description taken in conjunction with the drawings.

It will be recognized that some or all of the Figures are schematic representations for purposes of illustration and do not necessarily depict the actual relative sizes or locations of the elements shown.

DETAILED DESCRIPTION OF THE INVENTION

Figure 1:
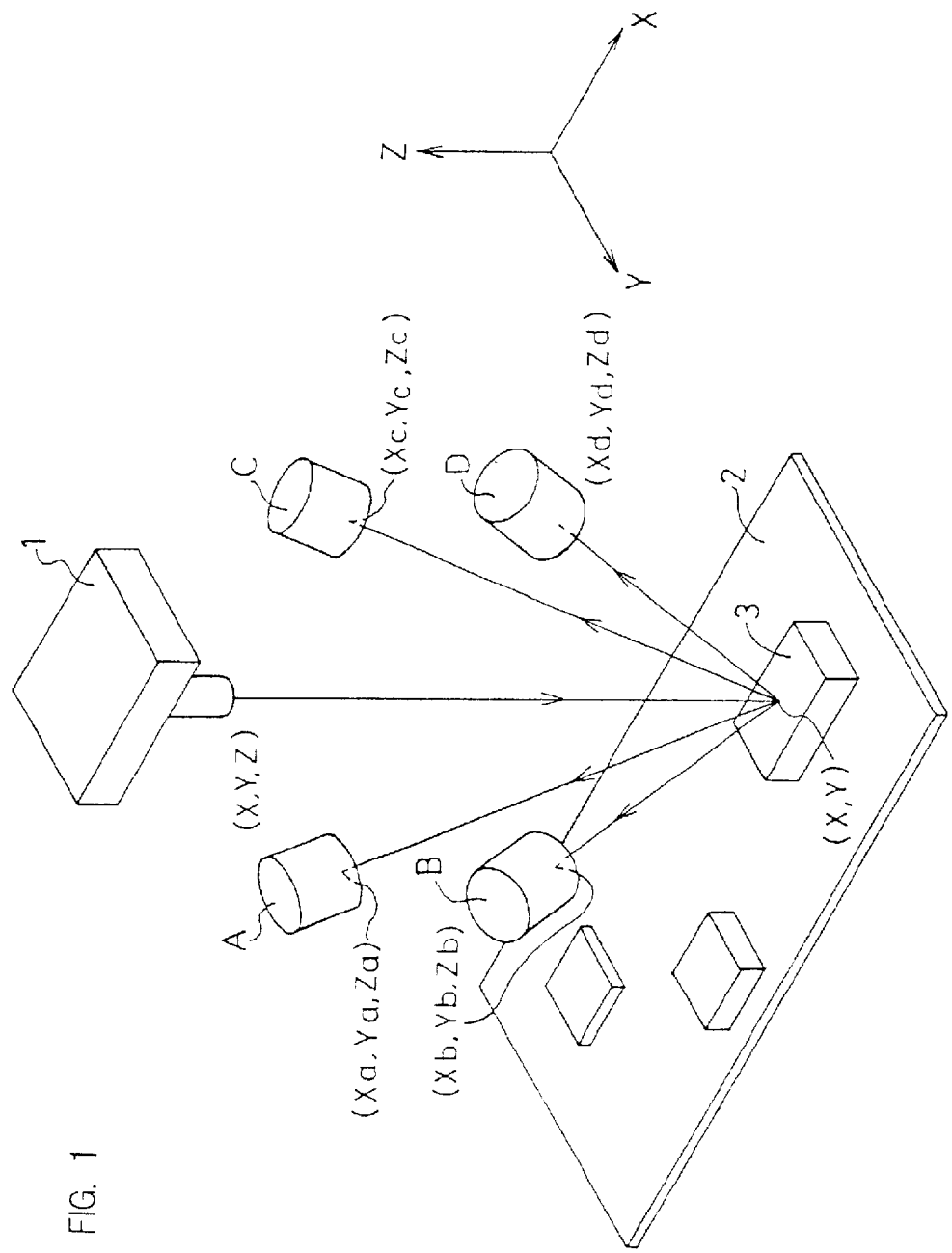
FIG. 1 is a drawing illustrating the operation of the surface-shape measuring apparatus used in the circuit board inspection method of the present invention.

In the following, preferred embodiments of the circuit board inspection method in accordance with the present invention are explained referring to attached drawings.
<<Embodiment 1>>
FIG. 1 is a drawing for illustrating the operation principle of a surface-shape measuring apparatus in the circuit board inspection method in accordance with the present invention. The surfaceshape measuring apparatus shown in FIG. 1 measures the surface-shape of a circuit board 6, which is a measurement object, based on the principle of trigonometric survey. This surface-shape measuring apparatus is constructed in a manner that a laser light L emitted from a laser unit 1 is projected on electronic parts 7 on a circuit board 2, and a reflected light thereof is received by four sensors. As these sensors, position sensitive detectors (PSD) A, B, C, and D which can distinguish the incident direction of the laser light, are used. The position sensitive detectors A, B, C, and D are such sensors that output two analogue signals responding to the position of receiving the laser light L.

From the principle of the trigonometric survey, using a light emitting source coordinate (X, Y, Z) of the laser light L, an illuminated position coordinate (X, Y) on an inspection object, laser light receiving coordinates (Xa, Ya, Za), (Xb, Yb, Zb), (Xc, Yc, Zc), (Xd, Yd, Zd), a height coordinate of the illuminated position on the inspection object is calculated.

By performing a conversion process on analogue signals issued from the position sensitive detectors A, B, C, and D, which are sensors, using equation (1), height data of the inspection object is calculated. In the following equations (1) and (2), $H(x,y)$ shows a measured height value at a sampling coordinate point $(x,y)$, and $B(x,y)$ is a measured brightness value (reflection intensity) at the sampling coordinate point $(x,y)$. And, $Ia(x,y)$ and $Ib(x,y)$ are signal values from respective sensors A, B, C, and D which are measured at sampling coordinate points $(x,y)$. By summing up two signal values $Ia(x,y)$ and $Ib(x,y)$ which are output signals of respective sensors, a brightness value $(B(x,y))$ at that sampling coordinate point $(x,y)$ is expressed as follows;

$$H(x,y)=Ia(x,y)/(Ia(x,y)+Ib(x,y)) \quad (1)$$

and $$B(x,y)=Ia(x,y)+Ib(x,y) \quad (2).$$

The measurement of the surface-shape data (height data) in a 2-dimensional space (inspection area) of an inspection object is performed by repeating it with fixing the sampling coordinate position and making a parallel translation movement of the inspection object in the XY coordinate plane, or by repeating it with fixing the inspection object and making a parallel translation movement of the sampling coordinate position.

As the method for measuring the surfaceshape data using apparatus other than mentioned above, there is, for example, the light-section method in which the height data are measured by the variation of slit light, or the stereo method in which the height data are measured from two or more than two parallax images, and it is also possible to obtain surfaceshape data from 3-dimensional data measured by such as X-ray CT apparatus (X-ray Computed Tomography System) or MRI (Magnetic Resonance Imaging System) apparatus.

Next, explanation is given on one example for performing a high accuracy inspection for the whole surface of a circuit board using data taken in the above-mentioned surface-shape measuring apparatus.

Figure 2:
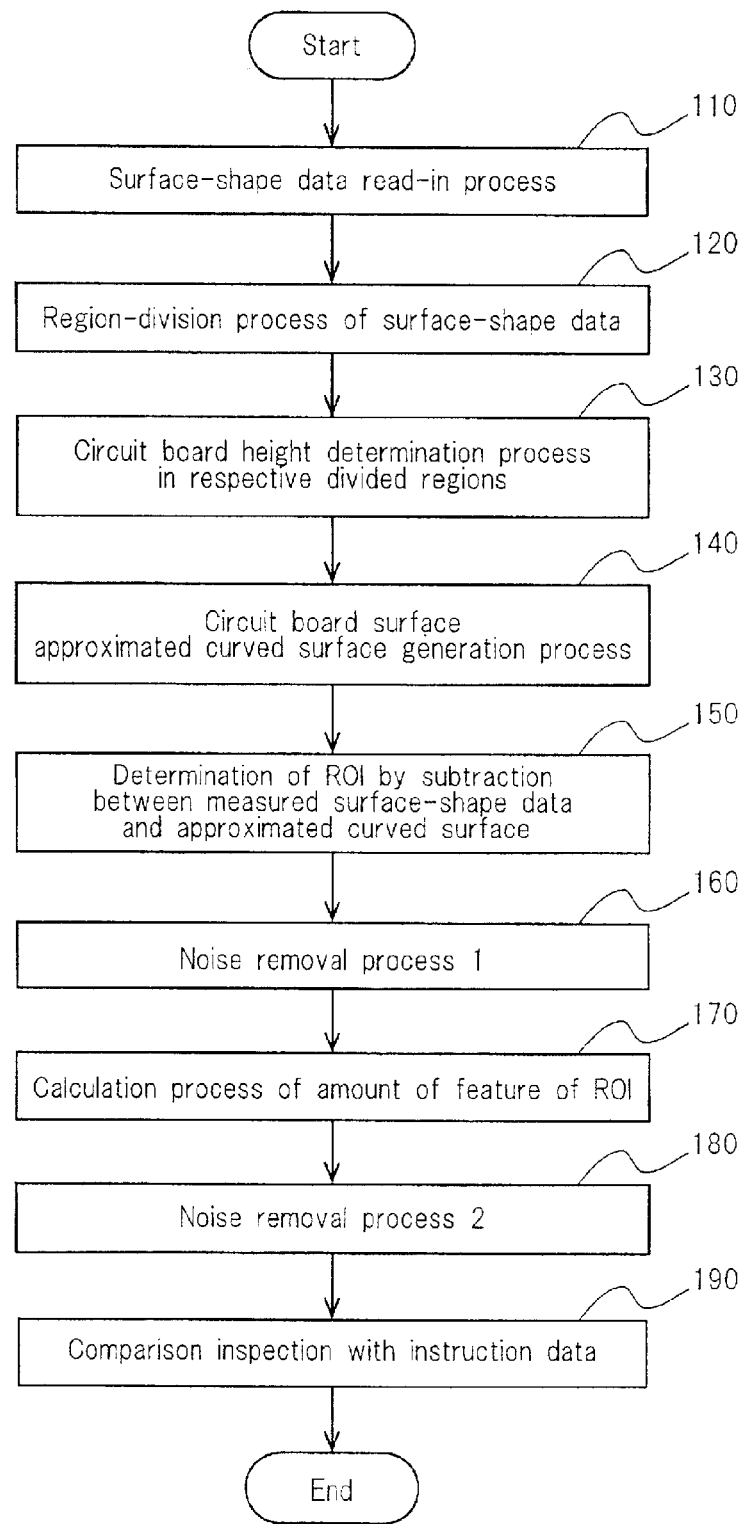
FIG. 2 is a flow chart showing an automatic inspection process of circuit boards in the circuit board inspection method of the present invention.

FIG. 2 is a flow chart showing the inspection process in a circuit board inspection method which is one mode of an embodiment in accordance with the present invention.

In step 110, measuring the surface-shape data of the circuit board as has been described above, then a process for reading in these surface-shape data is carried out. In step 120, the surface-shape data which were read in are divided into tile-shaped rectangular regions with a constant spacing in the XY plane. At this time, tile-shaped rectangular areas can also be set keeping an overlap with respect to the neighboring regions. As described above, by making these overlapping to the neighboring area, it becomes possible to get a further improvement in the approximation accuracy of the approximated curved surface. Hereupon, respective divided tile-shaped rectangular regions are set to be larger than the area of single piece of inspection objective parts in the horizontal plane.

In step 130, a process for determining respective height values in respective divided regions is carried out. Those circuit board height values obtained at this step 130 are determined as the height values at respective central coordinates of respective tile-shaped regions. A height value determination method will be described later.

In step 140, from the height values of respective circuit board regions determined discretely in step 130, the height values at coordinates between respective regions are calculated by a interpolation process. As a method of this interpolation process, assuming the parts installation surface of the circuit board to be a differentiable curved surface, a process is carried out using the third-order spline interpolation which generates a smooth approximated curves from discrete points. Hereupon, as for the interpolation process in the present invention, it is not limited to the third-order spline interpolation, and in order to realize a speed-up in the processing speed, process of 2-dimensional spline interpolation or one-dimensional spline interpolation can also be implemented. The height values in the whole circuit board surface calculated in such the ways as mentioned above is determined as an approximated curved surface of the circuit board.

In step 150, a subtraction process for subtracting the approximated curved surface calculated at the step 140 from the read-in surface-shape data read in at the step 110 is carried out. By this subtraction process, those regions which are higher than the approximated curved surface are determined as the ROI which is positioning on the circuit board. Hereupon, since various noises are included in the initial surface-shape data which were read in at the step 110, it is necessary to suppress these various noise data. For this, adding a constant offset value to the approximated curved surface data obtained by calculation, then thus obtained one is taken to be an approximated curved surface. And, in the step 150, by a subtraction process between this new approximated curved surface and the surface-shape data, the ROI is determined, and suppression of production of those noise regions can also become possible.

In step 160, in order to suppress the particle-shaped noise of the ROI determined at the step 150 as described above, as a first noise elimination process, performing reduction or expansion processes of regions, then the resulted region of this expansion or reduction is made to be a new inspection objective area. As for the reduction or expansion processes, an opening process of morphological filter or an closing process thereof is performed. By this process, reduction of the processing time of the next step 170 becomes possible.

In step 170, by performing a labeling process on the ROI determined at the step 150, a recognition process by a labeling process which performs a regional recognition is carried out. As for the recognition method, certain other method than the labeling method can also be used, for example, application such as region-growing process which is one of region expansion method is also possible. In step 170, characteristic numeric quantities expressing the features, such as main coordinates, area, volume, inclination, and a principal axis of the ROI where the recognition processing was performed are computed.

In step 140, although the approximated curved surface was generated by assuming the circuit board surface to be a differentiable curved surface, in actual circuit board, besides a circuit board region (actual installation region) through which the circuit board is to be installed on its product, a region for carrying purpose (carrying frame) is provided for the convenience of production purpose. This carrying frame is being removed at the time of assembling the product. As a result, a trench region is formed between the actual installation region and the carrying frame. In peripheral region in which this trench is formed, the circuit board is discontinuous, and the carrying frame are formed being lifted from the actual installation region. Consequently, the carrying frame becomes higher than the actual installation region, there is a risk by which this carrying frame is recognized faultily as ROI. To avoid any production of such the fault recognition, there is a necessity for reducing the region of the carrying frame. Therefore, in step 180, a second noise removing process is carried out, in which those regions such as the carrying frame which are preset regions excluded from the ROI are eliminated.

In step 190, the presetting characteristic numeric quantities expressing the features of parts to be installed on the circuit board at the normal condition as teaching data, then these teaching data and the numeric quantities expressing the features of the ROI are compared to each other. By this comparison process, inspection of parts installed on the circuit board is carried out.

Hereupon, in the above-mentioned inspection process flow, adding step 165 to the next of step 160, then by doing step 160 again, it becomes possible to determine the ROI in further higher accuracy.

In step 165, the ROI determined in step 150 is expansion-processed. In this microscopic region which was expansion-processed, the expanded ROI is separated to a ROI and a circuit board region. As a method for determining the threshold value for this separation, Otsu's process for conversion into two levels is used, in which a value giving maximum variance among classes in the histogram is determined as the threshold value. And, the region determined by this separation process is determined as a new ROI. In this manner, in step 165, in case that a difference between the approximated curved surface and the height of the inspection object is very small, the separation process is carried in the microscopic region, therefore a further high accurate determination of region becomes possible. After the process of step 165, step 160 is done once again, then it returns to the aforementioned step 170.

Figure 3:
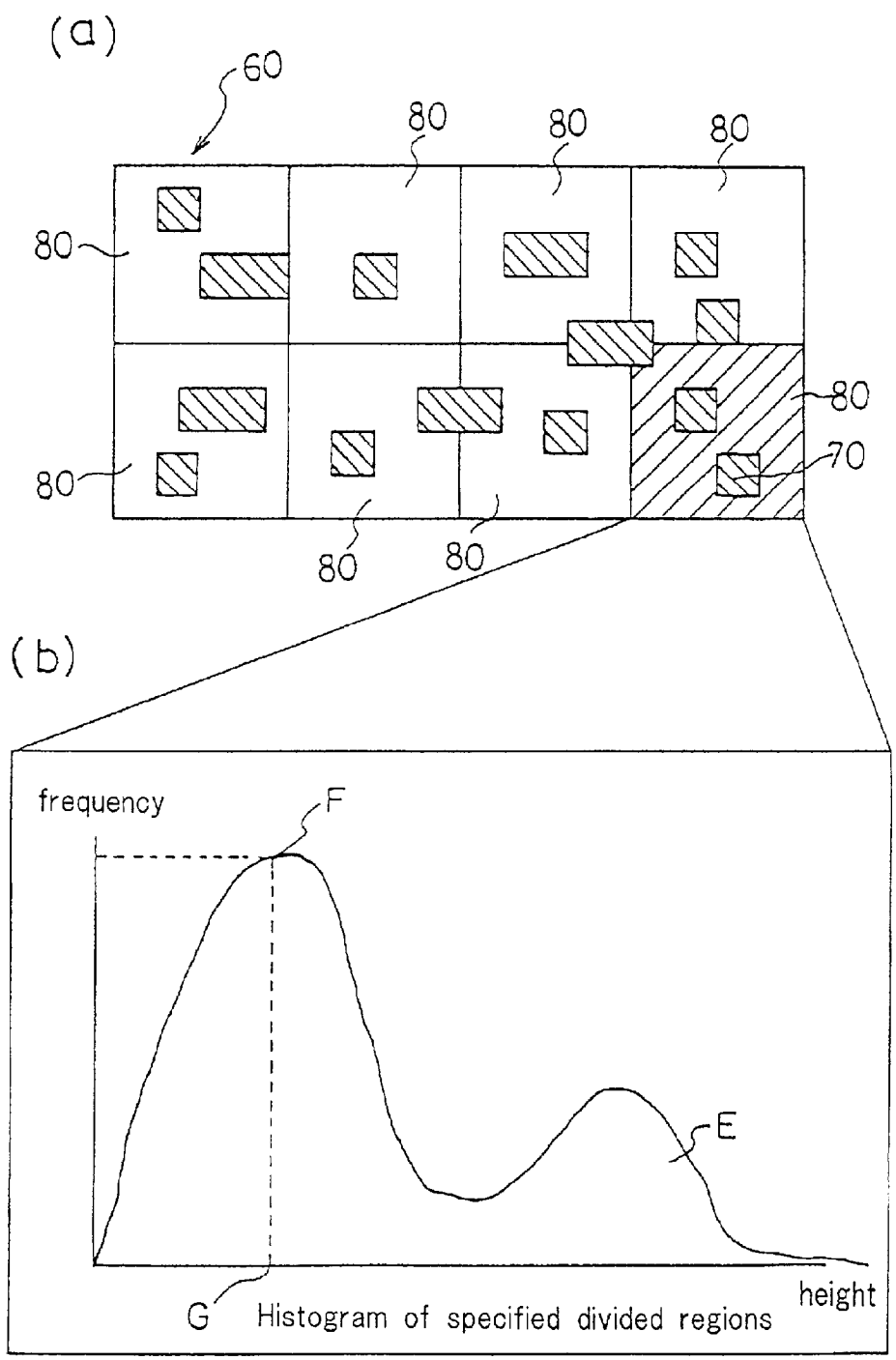
FIG. 3 is a drawing illustrating the circuit board surface automatic estimation method in the circuit board inspection method of the present invention.

Next, explanation is given on the method for determining the height value of the circuit board in the aforementioned step 130. FIG. 3 is a drawing for illustrating the method for determining the height value of the circuit board in divided respective regions, In the circuit board 60 shown in a part (a) of FIG. 3, a plural number of parts of interest 70 are placed. A method for determining the heights of the divided regions 80 is explained. The size of the divided regions 80 is set to be larger enough than the size of the largest part in the parts of interest 60.

At first, a histogram E in the surface-shape data of divided region 80 of the circuit board 60 is calculated. According to a histogram E shown in a part (b) of FIG. 3, at a height G of the surface of the circuit board 60 shown by the abscissa axis, frequency shown by the ordinate axis becomes a maximum value F. This height G is determined as the height of the divided regions 80 of the inspection objective, As the method for obtaining a maximum value abscissa, such a method that, a second-order curve is obtained from two points at before and behind of the maximum value, this curve is set to be an approximated curve, and then a maximum value of this approximated curve is determined as the maximum value of the histogram, or it is also possible to approximate whole the curve of the histogram and to determine the maximum value of this approximated curve to be a circuit board height. Further, it is possible to determine a region including such frequencies higher than a certain value, then setting the center of gravity of this region to be a maximum value abscissa of the histogram and to determine the height value at this abscissa value to be a height value of the circuit board.

In FIG. 3, although the inspection area is shown by an example of being divided into tile-shaped rectangular segments, It is also possible that these divided regions overlap with its adjacent inspection area and they are circular shape.

The process for generating and processing the histogram in the above-described mode of embodiment is effective in such the case in which the size of parts of interest is smaller than the area of the circuit board. However, conversely, in case that, in one divided region, the part of interest is very large with respect to the circuit board, then the maximum value of the histogram does not become equivalent to the height value of the circuit board, hence there was a problem that the height of the circuit board could not be estimated. Then, to solve such the problem, a circuit board inspection method which can automatically estimate the height of the circuit board without being influenced by the ratio of divided region and the ROI is explained below.

This circuit board inspection method is a method which generates masked data for only the particular parts in the divided regions, and generates a histogram of the surface-shape data at only these particular parts. The particular parts in the divided regions are such regions other than the ROI or regions on which copper-foiled (conductive pattern) planes which are placed the circuit board are existing.

By using the circuit board inspection apparatus which is so constituted as to perform the above-described circuit board inspection method, without being influenced by possible deformation of the circuit board by using an approximated curved surface which is the circuit board, a highly accurate recognition of the inspection objectives placed on the circuit board becomes possible, hence it becomes possible to realize a high accuracy inspection to the whole surface of the circuit board.

In the following, three different concrete inspection methods of the circuit board for automatically estimating the height of the circuit board are explained.

(1) Method Utilizing Reflected Intensity Data of The Laser Light from The Circuit Board In the surface-shape measuring apparatus shown in FIG. 1, as the characteristic of the reflected light intensity data, the measured reflected intensity data are changing depending on the surface state, the material, or the color of the illuminated bodies. Then, measuring and holding the reflected intensity from a particular positions beforehand, then a range of the reflected intensity values is specified in advance. Then at the time of generating the histogram, determining a range which is in the specified reflected intensity range, then a histogram in the surface-shape data of only those regions is generated. In general, at the copper-foiled surfaces have high reflected intensity values, whereas in the case that the surface colors of electronic parts such as IC's are black, their reflected intensity values are low.

As the automatically determining method of the reflected intensity values at the particular positions, producing a histogram in a region which is the identical to the divided regions of the surfaceshape data in the reflected intensity data, then a threshold by which the histogram region is divided into two regions is determined by using such as Otsu's two-level conversion method. Setting the determined threshold value to be a threshold value for dividing the regions into the copper-foiled (conductive pattern) regions showing higher reflected intensities and other regions than that, then a histogram of the surface-shape data showing reflected intensity values higher than the threshold value is generated. Thereby the histogram for the regions containing many copper-foiled planes is generated, the maximum values of this histogram is determined as the height values of the copper-foiled planes. And the heights of these copper-foiled planes are determined to be the heights of the circuit board plane.

(2) Method Utilizing The Color Information

A color image of the whole of the circuit board is taken by such as CCD camera. Then, the position matching process between this taken image and a 3-dimensional surface-shape data is carried out. This position matching process is made by, first, taking two or three points at reference marks placed on the circuit board as the reference, the affine conversion which quasi-converts coordinate points used in image processing. The surface-color of the circuit board is extracted from the color image, and then a histogram in the surface-shape data of only this extracted regions is generated. Hereupon, instead of performing the regional extraction of the surface-color of the whole of the circuit board as has been stated above, it is also possible to extract only the regions showing the copper-foiled surface color, or to extract those regions having colors other than the surface colors of parts.

(3) Method Utilizing The CAD Data

This method is a method which utilizes a CAD of the circuit board in place of the color information as in the above-described method (2). The processing contents of this method (3) can be done as in the identical processes in the above-described method (2).

Hereupon, in the circuit board inspection method of the present invention, it is also possible to use the above-described methods (1), (2), and (3) simultaneously, and by using them simultaneously, an inspection of further high accuracy the circuit board becomes possible. And by using a circuit board inspection apparatus which is so constructed as to be able to perform the above-described circuit board inspection method, high accuracy circuit board inspection becomes possible.

In the conventional circuit board inspection methods, those regions on which parts to be placed (instruction regions) are determined beforehand by users by hands, for these determined regions, the quantitative feature values of parts were set. In this manner, in the conventional circuit board inspection method, users determined the ROI by hands, and thereby the threshold values which were parameter values of the inspection reference data were produced. In contrast to this, in the circuit board inspection method of the present invention, it is possible that the ROI is automatically determined based on the information obtained in the fair circuit board, the threshold values which are parameters of respective parts in those inspection objective regions are set automatically.

In the conventional circuit board inspection apparatus, since only the ROI that the user specified was inspected, electronic parts placed faultily outside the regions or solder pastes or solders could not be detected. In contrast to this, in the circuit board inspection apparatus of the present invention, it becomes possible that, by estimating the installation surface of the circuit board, which is the inspection objective, automatically and in high accuracy from the measured surface-shape data, all of the parts installed on its surface are detected.

As conventional automatic approximation methods of the circuit board, method in which the circuit board surface was approximated to be a flat plane was proposed. However, actually the circuit board is being deformed, hence in case of inspecting (recognizing) such electronic parts or solders or soldering creams as being buried under this deformation, it was impossible to recognize in high accuracy by the flat plane approximation method. In contrast to this, in the present invention, it becomes possible to inspect parts in high accuracy without being dependent on the amount of the defamation by approximating the circuit board by a curved surface. And, in the automatic generation of this approximated curved surface, by an effective utilization of information such as the reflected intensity from the circuit board surface or the color information, and the CAD information, it is possible to generate a high-accuracy approximated curved surface for arbitrary inspection objective without depending on the size of the parts of interest.

As is obvious from the detailed explanation given above in the modes of the embodiments, the circuit board inspection method and its apparatus of the present invention have the following effects;

In accordance with the circuit board inspection method and its apparatus of the present invention, by an automatic and highly accurate estimation using the surface-shape data obtained by the measurement of the whole surface of the circuit board, it is possible to detect all of parts placed on the surface, therefore, it is also possible to perform the inspection for the outside of specified regions (inspection on the whole surface of the circuit board) which has been impossible by the conventional apparatus.

And, In accordance with the circuit board inspection method and its apparatus of the present invention, by an automatic recognition of all the part placed on the circuit board, and by applying these recognition data as the teaching data which are taken as the inspection reference data, setting of the part region which has been done by hands can be set automatically, and thereby a reduction in the setting time of the teaching data becomes possible.

Furthermore, in the board inspection method and its apparatus of the present invention, by approximating the circuit board by an curved surface, the part inspection can be done in high accuracy, and in the automatic generation of this approximated curved surface, by an effective utilization of information such as the reflected intensity from the surface of the circuit board or the color information, and the CAD information, it becomes possible to generate a high-accuracy approximated curved surface.

Although the invention has been explained on preferred embodiments with a certain extent of details, these present disclosed contents of preferred embodiments should be changed in small individual parts of the configuration, combinations and their orders of individual parts should be able to be realized without departing from the scope and spirit of the invention claimed.

What is claimed is:

1. A method for inspection of circuit boards comprising:
   process of measuring surface-shape data of a circuit board on which inspection objects are placed;
   approximated curved surface generation process for generating an approximated curved surface from the measured surface-shape data, which is an estimated surface-shape of the circuit board, on which no inspection object is placed;

process of subtracting said approximated curved surface generated from the measured surface-shape data;

region of interest determination process of determining regions which are different from the approximated curved surface in accordance with the data obtained by said subtraction process; and process of inspecting whether electronic parts placed on said circuit board and connecting materials for connecting the electronic parts are in a desired state or not.

2. A method for inspection of circuit boards according to claim 1, wherein said approximated curved surface generation process comprises:

histogram generation process in which measured data of the surface-shape of the circuit board are divided into small regions and a histogram in the measured data of the surface-shape of the respective divided regions is generated, circuit board height determination process for determining values of the circuit board heights at predetermined particular coordinate points in respective divided regions from the generated histogram, and process in which the height values at other coordinate points than said coordinate points at which the circuit board height values were determined am determined by an interpolation process using already determined height values, and thereby an approximated curved surface of the circuit board is generated.

3. A method for inspection of circuit boards according to claim 2, wherein said histogram generating process comprises:

process of measuring the reflected light amount from the circuit board, process of determining those regions that show a light amount of a particular intensity in measured reflected light amount data, and process of generating a histogram of the surface-shape data of particular regions using only those determined regions showing a particular intensity light amount.

4. A method for inspection of circuit boards according to claim 3, wherein said region determination process comprises:

process of generating a histogram in the reflected light amount data, process of determining a threshold value by which the histogram regions are divided from the generated histogram, process of region-dividing the reflected light amount data by the determined threshold value, and process of determining the regions of a particular light amount data from among divided regions.

5. A method for inspection of circuit boards according to claim 2, wherein said histogram generating process comprises:

process of measuring the color information of the circuit board, and process of generating a histogram of the surface-shape data of particular regions using only chose regions showing a particular color information in the measured color information.

6. A method for inspection of circuit boards according to claim 2, wherein said histogram generating process comprises process of generating a histogram of the surface-shape data of particular regions using only those particular regions in a computer aided design data of the circuit board.

7. A method for inspection of circuit boards according to claim 2, wherein said circuit board height determination process determines the maximum values of the histograms as the height values of the circuit board.

8. A method for inspection of circuit boards according to claim 2, wherein said circuit board height determination process calculates approximated curves of the histograms and determines its maximum values as circuit board height values.

9. A method for inspection of circuit boards according to claim 2, wherein, in process for getting the height values of the whole surface of the circuit board by said interpolation process, the whole surface of die circuit board is approximated by a curved surface by a higher-order interpolation process, and this is determined as an approximated curved surface of the circuit board.

10. A method for inspection of circuit boards according to claim 1, wherein, in said approximated curved surface generating process, a curved surface as a new approximated curved surface is obtained by adding an offset value to the generated approximated curved surface, then the subtraction process is performed by using this approximated curved surface.

11. A method for inspection of circuit boards according to claim 1, wherein, in said region of interest determination process, calculating a real value of respective region of interest obtained by said subtraction process, wherein only the real value that is in a predetermined range are determined as the region of interest.

12. A method for inspection of circuit boards according to claim 1, wherein said region of interest determination process comprises process of reduction and expansion, as well as eliminating minute regions with respect to respective region of interest obtained by said subtraction process.

13. A method for inspection of circuit boards according to claim 1, wherein region of interest determination process comprises:

process for expanding the region of interest, process of separating die expanded region of interest to a region of interest and a board surface region, and process of performing the inspection for the separated region of interest.

14. A method for inspection of circuit boards according to claim 1, wherein the region of interest determined in said region of interest determination process is made to be a teaching data which set an inspection reference.

15. A circuit board inspection apparatus comprising:

a measuring section for measuring surface-shape data of a circuit board on which inspection objects are placed;

an approximated curved surface generating section for generating an approximated curved surface which is estimating a surface-shape of the circuit board on which no inspection object is placed;

a subtraction section for subtracting the approximated curved surface from the measured surface-shape data;

an inspection objective-area determination section for determining regions which are different from the approximated curved surface as regions of interest in accordance with data obtained by said subtraction section; and an inspection section for inspecting whether electronic parts placed on the circuit board as well as connecting materials for connecting the electronic parts are in a desired state or not, with respect to the determined regions of interest.

16. A circuit board inspection apparatus according to claim 15, wherein said approximated curved surface generation section comprises:

a histogram generation processing section in which measured data of the surface-shape of the circuit board are divided into small regions and a histogram in the measured data of the surface-shape of the respective divided regions is generated, a circuit board height determination section for determining the circuit board heights at predetermined particular coordinate points in the respective divided regions from die generated histogram, and a processing section in which the height values at other coordinate points than said coordinate points at which the circuit board height values were determined are determined by an interpolation process using already determined height values, and thereby an approximated curved surface of the circuit board is generated.

17. A circuit board inspection apparatus according to claim 16, wherein said histogram generating processing section comprises; a processing section for measuring the reflected light amount from the circuit board, a region determination processing section for determining those regions that show a light amount of a particular intensity in measured reflected light amount data, and a processing section for generating a histogram of the surface-shape data of particular regions using only those particular regions showing a particular intensity light amount.

18. A circuit board inspection apparatus according to claim 16, wherein said histogram generating processing section comprises:

a processing section for measuring the reflected light amount from the circuit board, and a processing section for generating a histogram of the surface-shape data of the particular regions using only those regions showing a particular color information in the measured color information.

* * * * *